(12) United States Patent
Fillmore et al.

(10) Patent No.: US 6,316,181 B1
(45) Date of Patent: Nov. 13, 2001

(54) ESTABLISHMENT OF CELL LINES WITH PERSISTENT EXPRESSION OF A GREEN FLUORESCENT PROTEIN (GFP) USING A PIRES/EGFP DNA VECTOR CONSTRUCT

(75) Inventors: Helen Fillmore, Richmond; William C. Broaddus, Midlothian; John S. Shurm, Jr., Richmond; George T. Gillies, Charlottesville, all of VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 09/296,808

(22) Filed: Apr. 23, 1999

Related U.S. Application Data
(60) Provisional application No. 60/082,941, filed on Apr. 24, 1998.

(51) Int. Cl.[7] .............................. C12Q 1/02; C12Q 1/68; C12N 15/63; C12N 15/12; C12N 5/10
(52) U.S. Cl. .............................. 435/4; 435/6; 435/320.1; 435/325; 536/23.2; 536/24.1
(58) Field of Search .................................. 435/4, 6, 69.1, 435/455, 325, 320.1; 536/23.2, 24.1

(56) References Cited

PUBLICATIONS

Ha et al., Use of the green fluorescent proteing as a marker in transfected Leishmania, Molecular and Biochemiccal Parasitology 77 (1996).*

Valdivia et al. Applications for green fluorescent protein (GFP) in the study of host–pathogen interactions. Gene vol. 173 pp. 47–52, 1996.*

Plautz et al. Green fluorescent protein and its derivatives as versatile markers for gene expression in living *Drosophila melanogaster*, pland and mammalian cells. Gene vol. 173 pp. 83–87, 1996.*

Wang et al. Isolation of neuronal pr4ecursors by sorting embryonic forebrain transfected with GFP regulated by the Talpha 1 tubulin promoter. Nature Biotechnology vol. 16 pp. 196–201, 1998.*

Goldman et al. In vitro and in vivo gene delivery mediated by a synthetic polycationic amino polymer. Nature Biotechnology vol. 15 pp. 462–466, 1996.*

Clontech     http://www.clontech.com/chi–bin/citation Accessed Jan. 17, 2000.*

Muldoon et al. Tracking and Quantitation of Retroviral–Mediated Transfer Using a Completely Humanized, Red–shifted Green Fluorescent Protein Gene. Biotechniques vol. 22 pp. 162–167, 1997.*

Aboody–Guterman et al. Green fluorescent protein as a reporter for retrovirus and helper virus–free HSV–1 amplicon vector–mediated gene transfer into neural cells in culture and in vivo. Neuroreport vol. 8 pp. 3801–3808, 1997.*

Chalfie et al. Green fluorescent protein as a marker for gene expression. Science vol. 263 pp. 802–805, 1994.*

Lybarger et al. Rapid generation and flow cytometric analysis of stable GFP–expressing cells Cytometry vol. 25 pp. 211–220, 1996.*

Rees et al. Bicistronic vector for the creation of stable mammalian cell lines that predisposes all antibiotic–resistant cells to express ecombinant protein. Biotechniques vol. 20 pp. 102–110, 1996.*

DeClerck et al. Inhibition and metastasis in cells transfected with an inhibitor of metalloproteinases. Cancer Research vol. 52 pp. 701–708, 1992.*

Presley et al. ER–to–golgi transport visualized in living cells. Nature vol. 389 pp. 81–85, 1997.*

* cited by examiner

*Primary Examiner*—John S. Brusca
(74) *Attorney, Agent, or Firm*—McGuireWoods LLP

(57) ABSTRACT

The present invention provides a vector for stably transforming cells. The vector comprises the green fluorescent protein (GFP) from *Aequorea victoria* as a marker. The invention also provides stably transfected cell lines which may be used to assess real-time biological processes, including tumor cell migration.

25 Claims, 9 Drawing Sheets

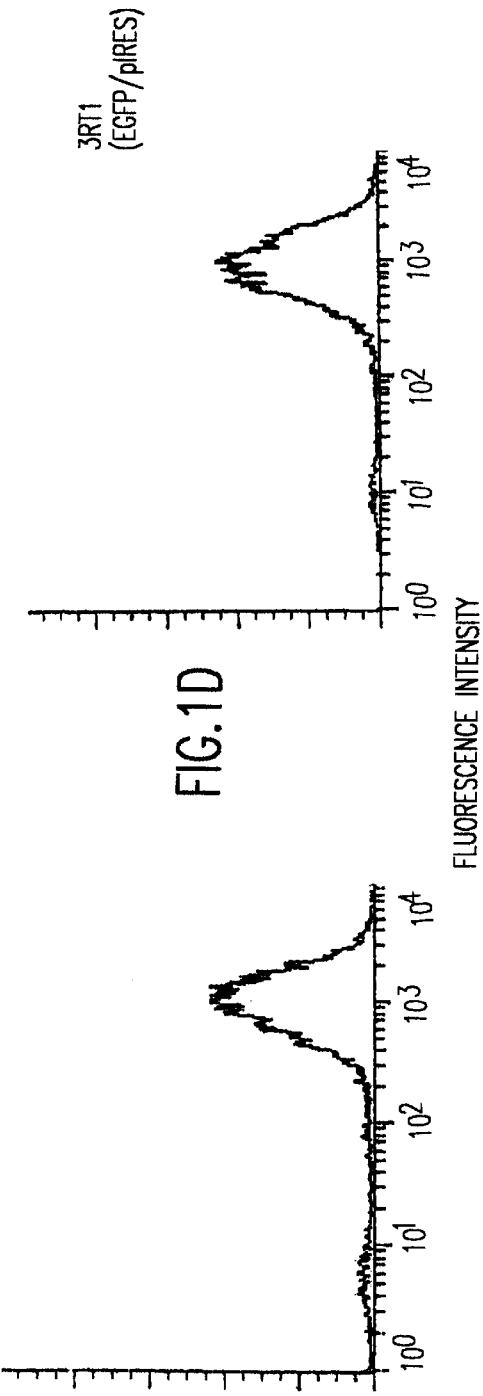

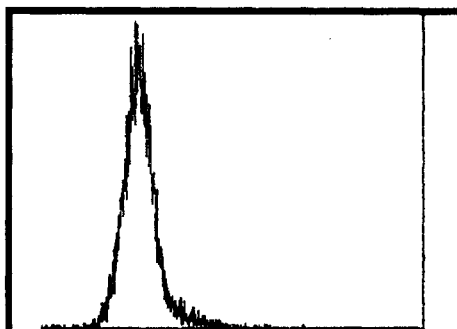
FIG.2A  RT2 PARENTAL CELL LINE
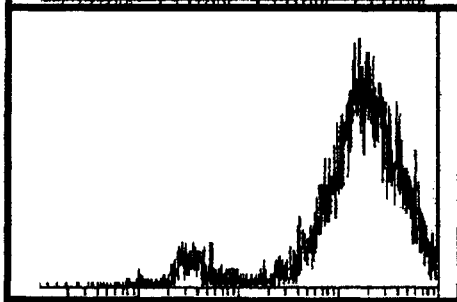
FIG.2B  3RT1 PASSAGE #3 − G418
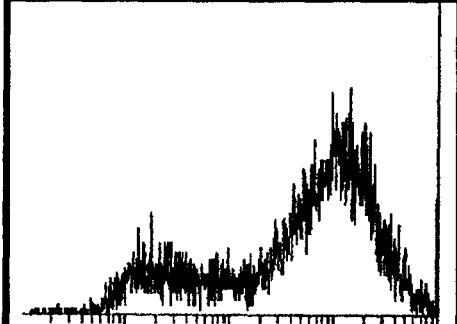
FIG.2C  3RT1 PASSAGE #9 − G418
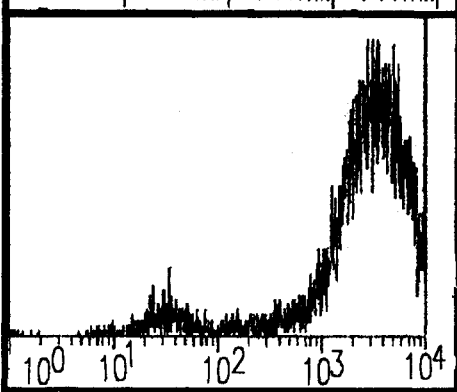
FIG.2D  3RT1 PASSAGE #9 + G418
FLUORESCENT INTENSITY

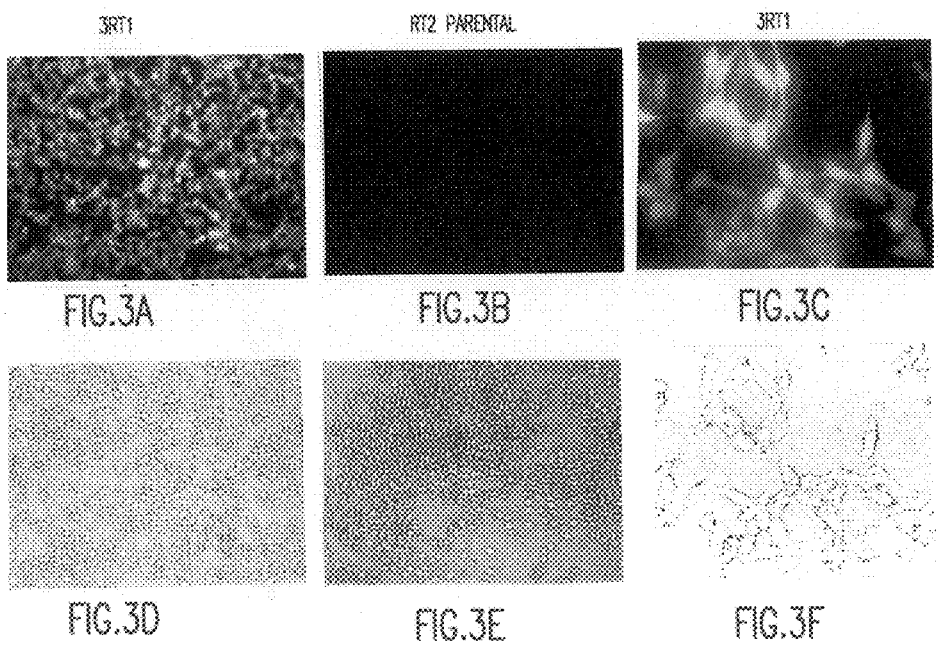

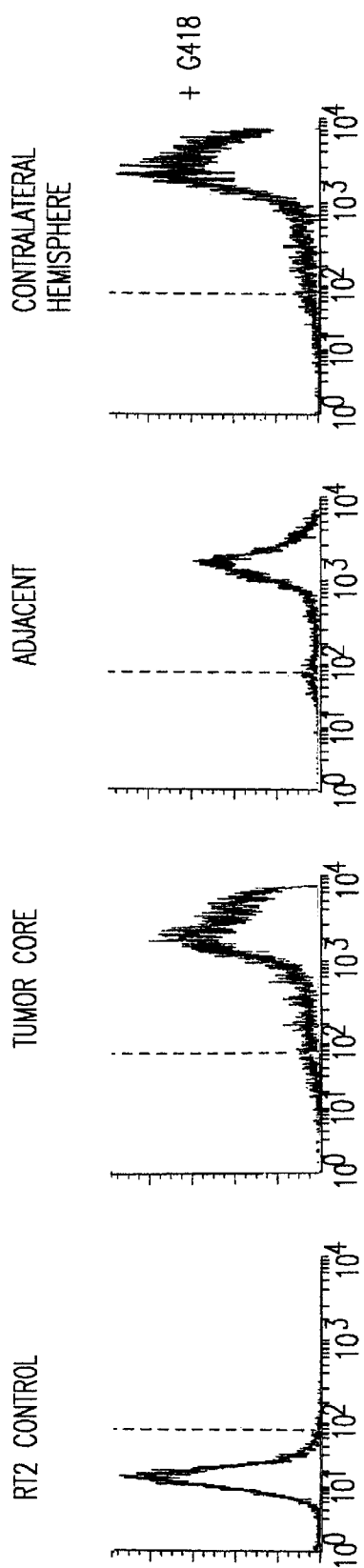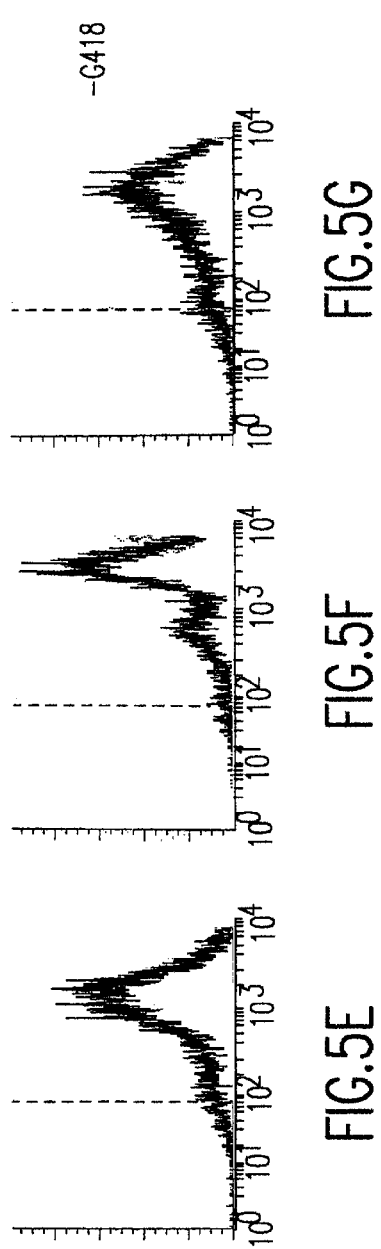

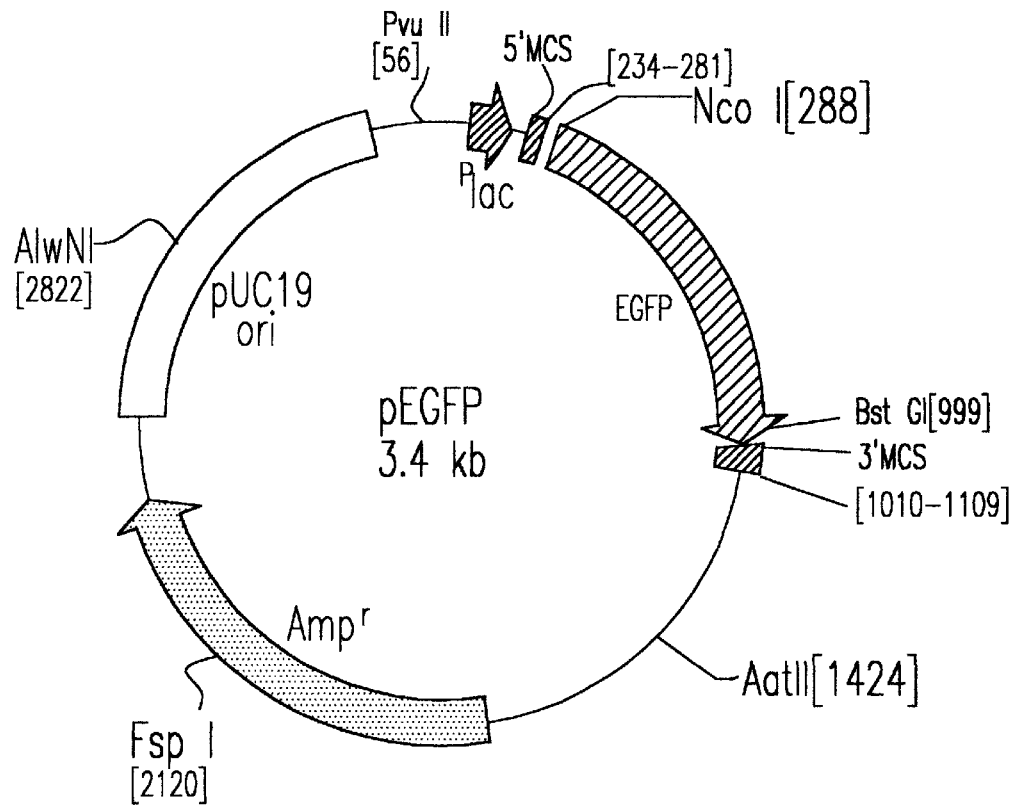

```
5' MCS
 lac Z      230         240         250         260         270         280         NOPP
ATG ACC ATG ATT ACG CCA AGC TTG CAT GCC TGC AGG TCG ACT CTA GAG GAT CCC CGG GTA CCG GTC GCC ACC ATG GTG
            Hind III  Sph I   Pst I   Acc I Xba I  BamH I Xma I Kpn I Age I       Nco I
                              Sal I                       Sna I Asp718 I
                              Hinc II
3'MCS
EGFP 1010
STOP
TAA AGCGGCCGCGACTCTAGAATTCCAACTGAGCGCCCGTCGCTACCATTACCAACTTGTCTGGTGTCAAAAATAATAGGCCT
    Not I  Xba I EcoR I                                                        Stu I 1080
ACTAGTCGGCCGTACGGGCCC
Spe I    BsiWI Bsp120 I
              Apa I
```

FIG.6

ESTABLISHMENT OF CELL LINES WITH PERSISTENT EXPRESSION OF A GREEN FLUORESCENT PROTEIN (GFP) USING A PIRES/EGFP DNA VECTOR CONSTRUCT

CROSS-REFERENCE TO RELATED APPLICATIONS

This patent application claims the benefit of provisional application filed Apr. 24, 1998 which is entitled: ESTABLISHMENT OF CELL LINES WITH PERSISTENT EXPRESSION OF A GREEN FLUORESCENT PROTEIN (GFP) USING A pIRES/EGFP DNA VECTOR CONSTRUCT having Ser. No. 60/082,941. The complete contents of that application is herein incorporated by reference.

DESCRIPTION

Abbreviations

GFP, green fluorescent protein; FACS, fluorescence activated cell sorting; PHAL, Phseolus vulgaris leucoagglutinin; DMEM Dulbecco's Modified Eagle Medium; FBS, fetal bovine serum; EDTA, ethylenediamine tetraacetic acid; PBS, phosphate buffered saline; IRES, internal ribosome entry sequence of the encephalomyocarditis virus; CMV, cytomegalovirus; NEO, neomycin.

BACKGROUND OF THE INVENTION

1. Field of the Invention

The invention generally relates to the establishment of cell lines which are stably transfected with a detectable marker. In particular, the invention provides a DNA vector carrying the GFP marker which can be used to establish stably transfected cell lines; to use for monitoring cell movement, proliferation, and location in vivo; and the invention pertains to stably transfected cell lines which include the GFP marker.

2. Background of the Invention

The ability to transfect cells with exogenous DNA and to monitor such genetically engineered cells in vivo is of fundamental importance to many areas of scientific investigation and emerging medical treatments. For example, ex vivo gene therapy for several diseases depends on the ability to transfect cells. In the treatment of Parkinson's disease, it is possible to surgically remove neural progenitor cells from the patient, grow them in culture, insert therapeutic genes, and then replace the transfected cells back into the patient's brain. However, the ability to monitor correct cell placement and gene expression, which would be a valuable addition to this treatment, is currently not available. Similarly, there is much interest in developing new cancer diagnostic tools to monitor tumor cell invasion, There are many ways to transfect cells with DNA. These include chemical transfections with lipids or lipid-type compounds, and shocking the cells by either chemical or electrical means. Another means of transfecting DNA into a cell is by using viral vectors (e.g. adenoviral and retroviral vectors) to transfect/transduce the host cells. However, with any of these techniques, the transfection of cells (whether mammalian, plant, or other type of cell) is usually transient, precluding long-term expression of the exogenous DNA or its gene products. For example, the use of viruses and dyes used to monitor cells are limited in that with subsequent cell divisions the ability of daughter cells to express the target DNA or dye diminishes with each cell division.

It would be highly desirable to have available a technique which would provide for the stable tranfection of cells. One important use of such stably transfected cells would be to monitor biological events in "real time". For example, it is currently not possible to detect the migration of cells such as brain tumor cells or neuronal stem cells. The provision of cells stably transformed with markers which allowed monitoring of biological events in real time would be highly advantageous.

One specific example of an area of medicine that would benefit from the ability to monitor real-time biological events is the field of brain tumor research, such as that involving glioblastoma multiforme, the most common primary brain tumor. Despite significant improvements in the diagnosis and treatment of patients with glioblastoma multiforme, it remains incurable. A key feature that underlies the malignant behavior of this disease is the ability of glioma cells to aggressively infiltrate surrounding brain tissue. Thus, understanding the basic biology of tumor cell invasion/migration may aid in the development of more effective forms of treatment [1–6].

Much information about glioma cell invasion has been gained from studies using a variety of in vivo and in viro models. Tumor cells have been labeled using Phaseolus vulgars leucoagglutinin (PHAL), cell labeling dyes, such as fast blue and transfection with the lacZ gene. Each technique has advantages and disadvantages [2, 7, 8 and references therein]. One disadvantage of using externally labeled cells is that long term studies (i.e. lasting multiple cell divisions) are difficult or impossible due to a decrease in signal over time. Although transfection with lacZ is stable, it requires post-processing using a chromogenic substrate for the β-galactosidase marker enzyme. Caution must be exercised when introducing dyes and substrate reagents into cells because this treatment can affect biological processes such as cell proliferation and motility [9, 10], the very processes one would like to observe.

It would be a distinct advantage to have available an improved means to monitor cell motility in general, and tumor cell migration in particular, e.g. to easily and rapidly identify tumor cells that are in the process of migrating, and to enable examination of their biochemical properties.

SUMMARY OF THE INVENTION

According to the present invention, cell lines have been stably transfected with a green fluorescent protein marker and used to monitor the migration of brain tumor cells. The vector that was used was the pIRES/EGFP vector. This vector was constructed from the commercially available vector pIRES FIG. 7) by inserting a gene coding for the green fluorescent protein (GFP) into the multiple cloning site of pIRES. The gene for GFP was obtained from the commercially available vector EGFP FIG. 8). These vectors and the details of the construction of pIRES/EGFP vector are further described in the Example section under Methods (DNA Constructs).

It is an object of this invention to provide a DNA vector capable of stably transforming cells. In a specific embodiment of the present invention, the vector is the construct pIRES/EGFP, and the form of the GFP protein that is provided is that which is in commercially available EGFP. However, the present invention also comprehends various other vectors which are derivatives of pIRES/EGFP. For example, it is a further object of the present invention to provide vectors with other mutational forms of GFP, such as a form with differing excitation and emission characteristics. Any suitable form of GFP which retains properties allowing it to be monitored after transfection into a cell may be used in the practice of the present invention.

The present invention also comprehends modifications of the vector. For example, another gene of interest may be ligated into the vector so that the expression of the gene of interest could be monitored simultaneously with monitoring cell motility. Or, inducible control elements may be added to the vector which confer the ability to control expression of the GFP protein. Any suitable modification of the vector which retains the ability of the cell transfected with the vector to be monitored in real time by tracking GFP fluorescence may be used in the practice of the present invention.

It is a further object of the present invention to provide cell lines which have been stably transformed with the vector pIRES/EGFP. In particular, the cell lines 3RT1 and U373GFP are provided by the instant invention. While these cell lines are of rat and human derivation, cell lines derived from any source (for example, plants) may be used in the practice of the present invention.

It is an object of the present invention to provide cell lines stably transfected with a green fluorescent protein as reagents for asessing tumor cell migration. It is a further object of the present invention to provide the cell lines transfected with a green fluorescent protein to be utilized for the real-time assessment of other biological processes and events. Those of skill in the art will recognize that the cell lines of the present invention may be utilized for the assessment of any suitable biological process or event.

It is an object of the present invention to provide glioma cells which have been stably transfected with the vector pIRES/EGFP. It is a further object of the present invention to provide a method for stably transfecting other cell types with the vector pIRES/EGFP. For example, neuronal stem cells from both human and rat could be transfected to include a GFP marker. Those of skill in the art will recognize that cell lines from any tissue source may be used in the practice of the present invention.

BRIEF DESCRIPTION OF THE DRAWINGS

FIGS. 1A–D: Flow cytometric analysis of RT2 parental and an EGFP/pIRES transfected RT2 cell clone, 3RT1, at initial and passage number 21. A: RT2 parental at initial passage; B: RT2 parental at passage 21; C: EGFP/pIRES transfected RT2 cell clone at initial passage; D: EGFP/pIRES transfected RT2 cell clone at passage 21.

FIGS. 2A–D: Flow cytometric analysis of RT2 parental and the EGFP/pIRES transfected clone, 3RT1 in the absence or presence of G418 selection medium. 2A) RT2 parental cell line; 2B) 3RT1 passage #3 without G418; 2C) 3RT1 passage #9 without g418; 2D) 3RT1 passage #9 with G418.

FIGS. 3A–F: Fluorescence and phase contrast photomicrographs of unfixed in vitro RT2 parental cells (B and E) and cells derived from a EGFP/pIRES-transfected (3RT1) clone (A and D, and C and F). Fluorescence and phase contrast photographs were taken from corresponding fields through a 10×(A,B,D, and E) or 40×(C and F) objective.

FIGS. 5A–G. Flow cytometric analysis of RT2 parental control cells (7A) and GFP positive cells B–G) isolated by fluorescence-activated cell sorting from rat brains harboring EGFP/pIRES transfected glioma cells. GFP positive cells were cultured with G418 (B, C and D) or withour G418 (E,F and G). The GFP positive cells had been isolated from the tumor core (B and E), form adjacent tissue (C and F) and from the contralateral hemisphere (D and G).

FIG. 6. Schematic representation of the pEGFP vector (SEQ ID NOS:1 and 2).

DETAILED DESCRIPTION OF THE PREFERRED EMBODIMENTS OF THE INVENTION

Figure 4:
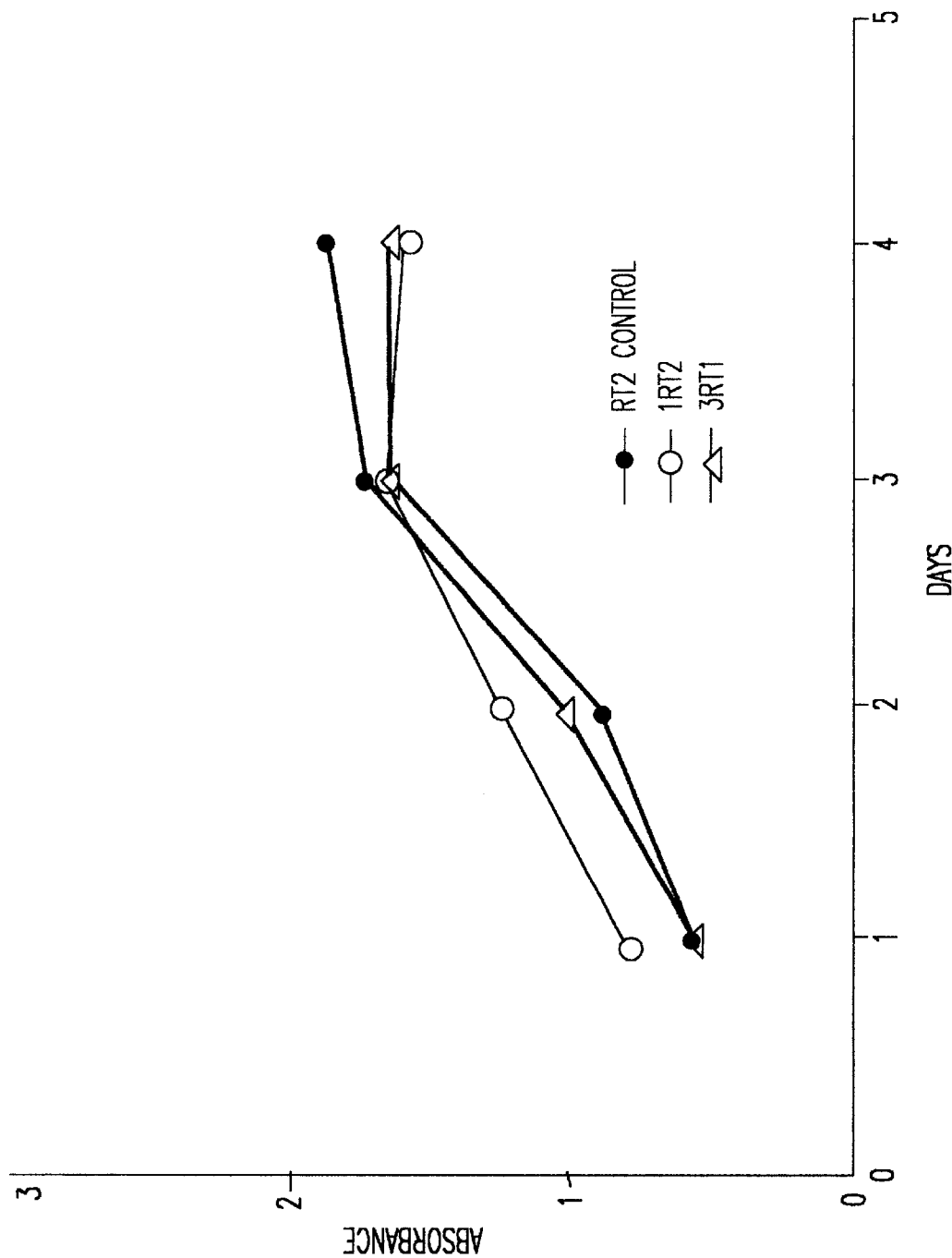
FIG. 4: MS proliferation assay comparing growth rates of parental RT2 and EGFP/pIRES transfected (3RT1) rat glioma cells.
Figure 7:
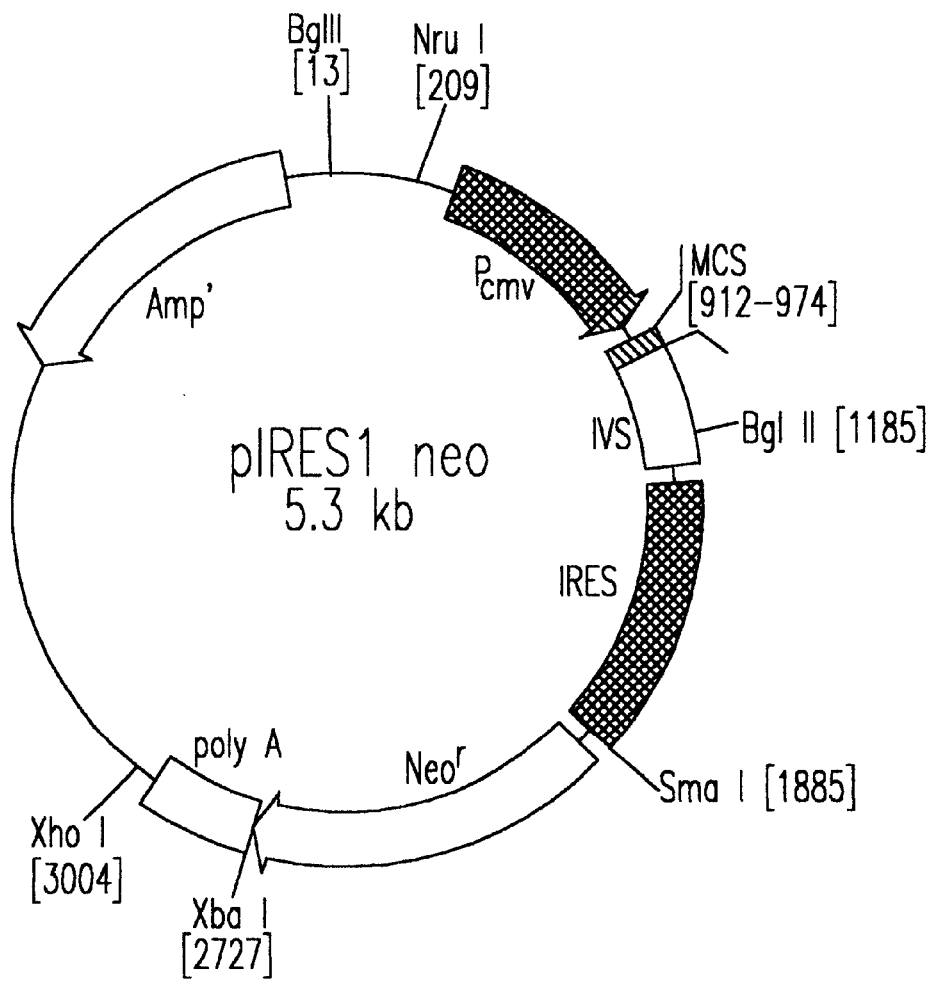
FIG. 7. Schematic representation of the pIRES neo vector (SEQ ID NO:3).

The vector pIRES/GFP which was utilized in a preferred embodiment of the present invention is that which is described in the Examples section under Methods (DNA Constructs). However, it will be readily comprehended by those of skill in the art that the vector pIRES/EGFP maybe modified in several ways within the scope of this invention. For example, the vector may be modified to include another gene of interest in addition to GFP such as the tissue inhibitor of matrix metalloprotemase (TIBE) gene or the tyrosine hydroxylase gene which is associated with Parkdnson's disease. Any appropriate gene of interest may be ligated into the vector in a manner so as to effect its expression. Other genes of interest may be ligated into the multiple cloning site of pIRES/EGFP so that they will be co-transcribed as fusion proteins, or in a manner so that they are transcribed (in entirety) independently from GFP. The independent transcription may be constituitive or inducible. In addition, the vector may be modified to include control elements which are directed to the expression of the GFP protein, making it possible to selectively induce the expression of GFP. The vector may also be modified to include genetically based signals which direct or target the vector to cells of interest. An example of another gene of interest that may be included in the pIRES/EGFP vector is the Nestin promoter of neuronal stem cells. Also, another modification which is comprehended by the present invention is the cloning of the fragment of pIRES/GFP which contains only the pIRES and GFP genes into a suitable viral vector such as a retrovirus or replication deficient adenovirus. The techniques necessary for manipulating DNA vectors and cloned genes to carry out such modifications (e.g. digestion with restrction enzymes to remove a selected portion of a vector or cloned gene, and religation of the selected portion into another vector) are readily available and well known to those of skill in the art.

The stable marker in the cell lines of a preferred embodiment of the present invention is the GFP marker as provided in vector EGFP. However, those of skill in the art will recognize that modifications of the GFP protein other than that provided in commercially available EGFP may be utilized in the practice of the present invention. For example, other mutations of GFP that differ in excitation and emission characteristics may be used in the practice of the present invention, either alone or in combination with the form of GFP in pIRES/EGFP. Any suitable form of GFP may be used in the practice of the present invention.

In a preferred embodiment of the present invention, the transfection was carried out using the reagent "LIPO- FECTAMINE™" (for description, see Methods: Cell Culture, Transfection, and Subcloning in the Examples section). However, it will be readily understood by those of skill in the art that other means of transfection may be utilized in the practice of the present invention. For example, transfection may be accomplished with other lipid-type compounds, by chemical or electrical means, or by the use of viral vectors such as a retrovirus or replication deficient adenovirus. Any suitable means of transfection may be utilized in the practice of the present invention.

In preferred embodiments of the present invention, the cells which were stably transfected were glioma cells derived from rats and human cell lines. However, it will be readily understood by one of skill in the art that cells derived form other species and from other cell or tissue types may be stably transfected by the practice of this invention. For example, cells derived from other mammalian species (e.g., human) or cells derived from plant species may be utilized in the practice of the present invention. In addition, cells may be derived from, for example, neuronal stem cell progenitor cells. In the practice of the present invention, the cells which are stably transfected may be derived from any suitable tissue or cell type from any appropriate species.

The present invention provides a means to assess cell motility. In a preferred embodiment of the present invention, an improved means to monitor tumor cell migration, to easily and rapidly identify tumor cells that are in the process of migrating, and to enable examination of their biochemical properties is provided. However, it will be understood by those of sill in the art that the practice of the present invention is not confined to the observation of cell motility such as tumor cell migration. The practice of the present invention may be used to monitor any appropriate biological process and/or event in real time. The biological processes or events monitored in the practice of the present invention may be either in vivo or in viro. For example, the effects of candidate drugs during product testing, infectious agents, toxins, contaminating organisms, etc. on host tissue and cells may be monitored in real time by the practice of the present invention. In this application, a cell line transfected with a GFP marker is exposed to a pharmaceutical, an infectious agent (e.g. a virus), toxin or contaminating microorganism and the effects can be readily monitored.

In a preferred embodiment of the present invention, the means of detecting the presence of GFP in the stably transfected cells is by fluorescence incroscopy and by FACS. However, it will be readily understood by those of skill in the art that other means for detecting the presence of GFP may also be used in the practice of the present invention. The means of detecting GFP or of tracking or monitoring cells which have been stably transfected with a pIRES/EGFP construct (or variation of the pIRES/EGFP construct) may be any means whereby the presence GFP protein is detectable. For example, optical imaging, infrared imaging of gene expression and flow cytometry may also be used.

The present invention provides cell lines that are stably transfected with the green fluorescent protein (GFP) marker. The use of these cell lines makes possible real time observation of biological events in vivo. The cells can be monitored long-term (i.e. after indefinite cell divisions) without the need for histochemical or immunochemical treatment. However, it will be recognized by those of skill in the art that histochemical and immunochemical treatments may also be used in conjunction with the methods of the present invention. For example, if a second gene of interest is incorporated into the pIRES/EGFP vector, any appropriate means of detecting the presence of that gene may also be used in the practice of the present invention.

The cell lines of the present invention may be utilized as reagents for assessing tumor cell migration. As such, the cell lines may be provided either frozen or as live cells from an approved cell culture depository such as the American Type Culture Collection (ATCC). Methods of culturing freezing and shipping of cell lines are well known to those in the art.

The cell lines may be used in many lines of investigation in which it is desirable to monitor such phenomena as cell migration, proliferation, location, apoptosis, cell shape and changes in cell shape, in response to a variety of experimental paradigms. For example, using the cell lines of the present invention, it would be possible to monitor changes in cellular location in vivo and to correlate those changes with the expression of a particular protein of interest by utilizing antibodies to the protein of interest. The methods of the present invention would provide the ability to insert the cell lines of the present invention into an in vivo model (e.g. a rat), locate and retrieve the cells, and determine whether the protein of interest has been expressed at the particular location from which the cells were retrieved. This could be useful to investigate the expression of such proteins as the integrin proteins during tumor cell migration.

The cells of the present invention could be used to monitor infectious agents, for example, trypanosomes. After stably transfecting the trypanosomes with the vector of the present invention, the life cycle of the trypanosome could be monitored in vivo (i.e. after infecting a host organism such as a rat with the transfected trypanosomes) or in culture if the trypanosomes were being maintained in culture in a lab. The location and movement of these infectious organisms could than be traced with relative ease. In addition, the effect of drugs on the trypanosomes could be readily monitored. After administration of a drug (either to the in vivo host, or to the trypanosome culture), the effects of the drug with respect to trypanosome motility, location within the host, or the related expression of other genes, could be monitored by retrieving the GFP marked cells. Trypanosome cultures and the methods of culturing such disease agents are readily available and well established.

The cell lines of the present invention could be utilized to investigate various aspects of the cell cycle. FIG. 4 presents data obtained with cell lines of the present invention with respect to proliferation, showing that cells stably transfected with pIRES/EGFP proliferate at a rate similar to that of the control cells. Thus, the transfected cells of the present invention could, for example, be tested with various agents known to affect cell cycling (e.g. those known to arrest cells at a particular stage of the cell cycle) and the effect of such arrest could be correlated to cell motility, cell shape, or other appropriate parameter. The methods for arresting the cell cycle at various stages are well known to those of skill in the art. Alternatively, GFP stably transfected cells may be retrieved as live cells from a host and their cell cycle profile could be determined in terms of location in the host.

The vector of the present invention could be useful in identifying which gene products are necessary for a given cellular phenomenon, such as tumor cell mobility. The vector of the present invention could be used to stably transfect two related tumor cell types which differ only in the expression of a single protein, for example an integrin protein. Both cell types could then be inoculated into an animal model, and the patterns of migration and the relative levels of invasiveness of the two cell types could be tracked and monitored in vivo.

In addition, the vector pIRES/EGFP itself, or suitable derivatives of this vector, may be provided directly as a reagent for stably transfecting cell lines. Methods for providing and using DNA vectors are well-known to those of skill in the art.

In the experiments which are presented in the Examples below, we show that the stable transfection of glioma cells with GFP does not alter either the in vivo or in vitro growth characteristics of the cells. We show that, in rat brain, migrating tumor cells can be detected in brain sections without histological treatment of the tissue. We also demonstrate that the invading glioma cells can be retrieved by fluorescence activated cell sorting (FACS) for further biochemical and molecular characterization. These examples merely illustrate several aspects of the invention, and should not be interpreted in any way to restrict the applications of the invention.

EXAMPLES

Methods

DNA Constructs

Figure 8A:
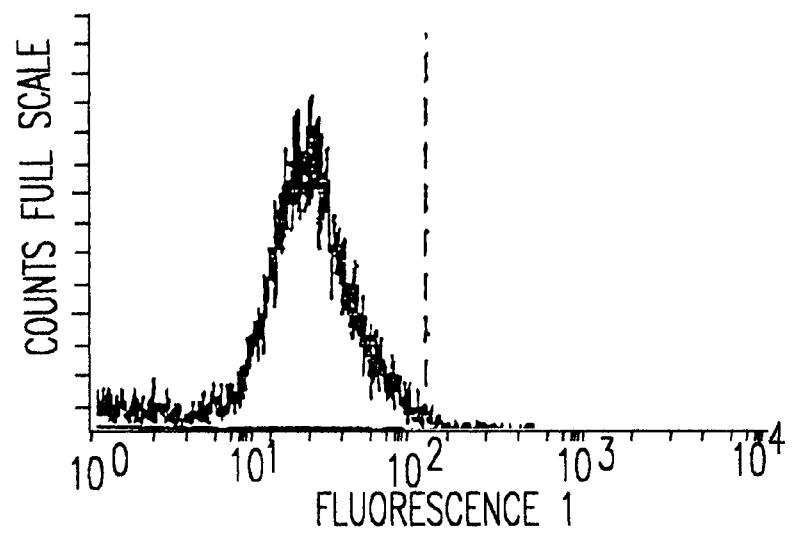
FIGS. 8A–B. Flow cytometric analysis of U373 parental human glioma cells and an EGFP/pIRES transfected U373 cell clone, U373-GFP, at passage number 3.
Figure 8B:
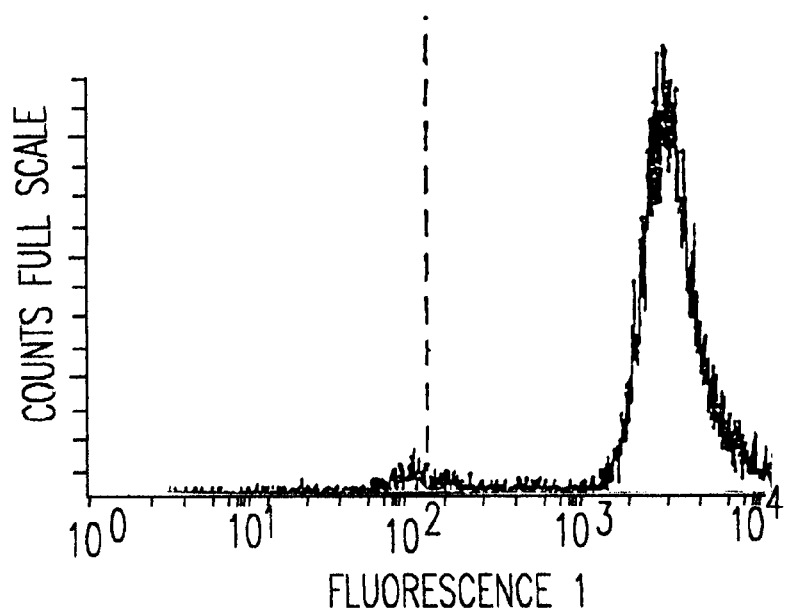
Figure 9A:
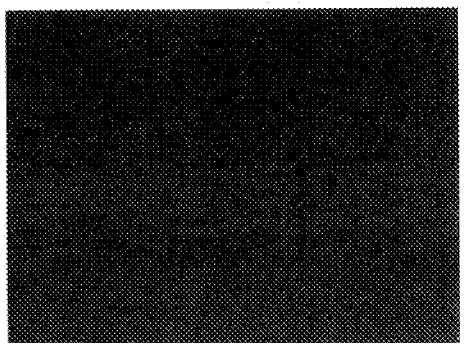
FIG. 9A–D. Fluorescence photomicrographs of unfixed in vitro U373 parental human glioma cells (13) and cells derived from a EGFP/pIRES-transfected (U373-GF) clone (A); and phase contrast photomicrographs of unfixed in vitro U373 parental cells (D) and cells derived from a EGFP/pIRES-transfected (U373-GFP) clone (C), Fluorescence and phase contrast photographs were taken from corresponding fields through a 10× objective.
Figure 9B:
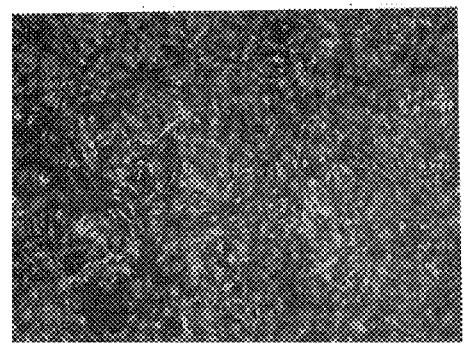
Figure 9C:
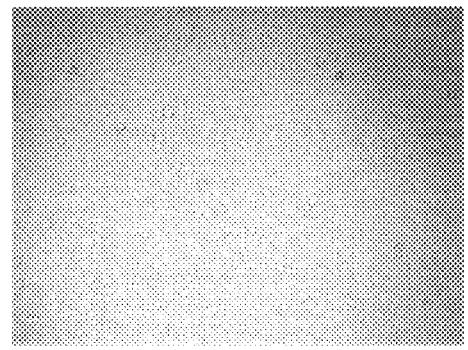
Figure 9D:
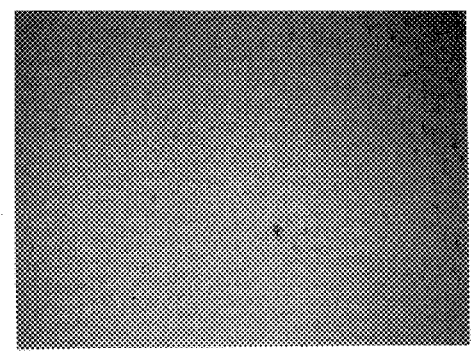

The vectors pEGFP (FIG. 8) and pIRES neo FIG. 9) were purchased from Clontech (Palo Alto, Calif.). The pEGFP is a form of the GFP protein from the Aequorea Victoria jellyfish; cloning of the GFP protein and the subsequent variations thereof have made the GFP a powerful reporter gene for a wide range of experimental designs (11–19). The GFP of pEGFP has been modified to be brighter than native GFP (excitation maxima 488 nm; emission maxima 507 nm) and has been "humanized" (contains more than 190 silent base changes that correspond to the human codon-usage preference and upstream flanking sequences converted to a Kozak consensus translation initiation site). The EGFP coding sequence was isolated by digestion of the pEGFP vector with the restriction enzymes Hinc II (blunt end cutter) and Not I and ligated into the pIRES neo vector which was digested with EcorV (blunt end cutter) and Not I, therefore creating the construct we term EGFP/pIRES. The advantage of using the pIRES vector is that it contains the internal ribosome entry site of the encephalomyocarditis virus, which allows for the translation of two open reading frames from one messenger RNk In this experimental design the EGFP and the NEO resistant gene are co-translated as a result of integration of a single vector construct. In addition, the pIRES bicistronic expression vector contains the human cytomegalovirus (CMV) promoter.

Cell Culture, Transfection, and Subcloning.

RT2 parental cells were a gift to W. C. Broaddus from Dr. G. Y. Gillespie, University of Alabama at Birmingham. They were dervied from a glioma induced by the inoculation of the Rous sarcoma virus into the brains of prenatal Fisher 344 rats. Human U373 glioma cells were obtained from the American Type Culture Collection. The cells were cultured in DMEM (Life Technologies, Inc.) containing 10%/ FBS (Life Technologies, Inc), non-essential amino acids (Cellgro), 2 mM L-glutamine (Life Technologies, Inc), penicillin-streptomycin (100 units/ml and 100 mg/ml) (Life Technologies, Inc), and 50 $\mu$g/ml gentanmicin sulfate (Biowhittaker). A mixture of 4.17 mg of pCMV-EGFP (EGFP/pIRES) vector and 50 mg "LIPOFECTAMINE™" reagent in 200 ml serum-free medium was used for transfection (Life Technologies, Inc.). "LIPOFECTAMINE™" is a 3:1 liposome formulation of the polycationic lipid 2,3-dioleyloxy-N-[2(spermine-carboxamido)ethyl]-N,N-dimethyl-1-propanaminumtrifluoroacetate and the neutral lipid dioleoyl phosphatidylethanolamine in membrane filtered water, and is commercially available from Gibco. RT2 cells were overlaid with the mixture at 80% confluence and incubated at 37° C. in 5% $CO_2$ for 5 hours before being replenished with 10% DMEM. RT2 cells were harvested by 0.025% trypsin/EDTA 64 hrs post-transfection and subcultured in selective medium containing 1 mg/ml G418 (Geneticin Antimycotic medium, available from Gibco). Clones were isolated with cloning cylinders Fisher Scientific) by trypsin/EDTA. Conventional cell culture methods were used to transfer and amplify the clones.

MTS Assay

The CellTiter96 Aqueous cell proliferation assay purchased from Promega Madison, Wis.) was used for glioma cell proliferation studies. The amount of formazan product (490 nm absorbance) made from the conversion of MTS by dehydrogenase enzymes of metabolically active cells is directly proportional to the number of living cells in culture. MTS tetrazolium compound (Owen's reagent) is [3-(4,5-dimethylthiazol-2-yl)-5(3-carboxymethoxyphenyl)-2(4-sulfophenyl)-2H-tetrazollum, inner salt. Cells (500 or 1000/well) were plated into 96 well plates and allowed to grow for 4 to 7 days. GFP transfected RT2 cells were compared with control non-transfected RT2 cells.

Flow Cytometry and Cell Sorting

Flow cytometric analysis was performed using a Becton Dickinson FacScan, using $1 \times 10^6$ cells/ml in PBS. Gating of viable cells was based on particle size and light scatter. Fluorescence activated cell sorting (FACS) was performed using a Coulter EPICS Elite ESP using a 100 micron sort-sense quartz tip. The fluorescence was excited with the 488 nanometer emission of the standard air-cooled argon laser. All fluorescence emission was filtered with a 488 nm laser blocking filter followed by a 550 nm dichroic long pass filter. GFP (green) fluorescence was further filtered with a 525 nm bandpass filter. Data was acquired in single and dual parameter histograms with appropriate light scatter and fluorescence gating, both in real time and in list mode. Fluorescence data was acquired in both log and linear modes. For cell sorting experiments the highly fluorescent green populations were physically isolated by using Coulter's standard Autoclone assembly to sort 3000 cells per well directly into media-filled 24 well plates.

Microscopy

Fluorescence and light microscopy were performed using a Nikon Eclipse. E800 nicroscope and a GFP filter set made by Chroma Technology Corporation (Brattleboro, Vt.).

Animal Experiments

Female Fisher 344 rats, (150 to 160 g), were anesthetized using an intraperitoneal injection of ketamine (50–80 mg/kg) and xylazine (5–10 mg/kg). After induction of anesthesia, the animals were mounted on a stereotactic frame, and a burr hole was made 3.5 mm lateral and 1 mm posterior to the bregma. A 25-guage needle was advanced to a depth of 4.5 mm and then a 5 ml suspension containing 10,000 RT2 or RT2 -GFP tumor cells in artificial cerebrospinal fluid was infused into the caudate/putamen. The rats were sacrificed 14 days post tumor cell infusion for biochemical analysis of GFP fluorescence.

Preparation of Single Cell Suspension from Fresh Tissue.

Single cell suspensions were prepared using DAKO's Medimachine and accessories (Carpinteria, Calif.). For cell sorting experiments, brains containing EGFP/pIRES RT2 cells were taken from sacrificed rats, and placed on ice cold PBS. Hemispheres were separated using a surgical blade and the contralateral hemisphere was set aside and placed in separate petri dish in PBS on ice. Tumor core was cut and also placed in separate petri dish in PBS on ice. Each sample of contralateral hemisphere, adjacent tissue and tumor core was cut into small pieces using separate blades. For each sample, the tissue pieces were placed on a pre-wetted (1 ml PBS) medicon (DAKO). After replacing the top of the medicon, the medicon was inserted into the medimachine and allowed to mechanically disaggregate the tissue samples for 30 seconds to 1 minute. Following the collection of the dissociated cells using a 1 ml syringe, the medicon was washed with 1 ml ice cold PBS and run through the medimachine once again. Following the second collection of the washed and remaining calls, the cells were combined and pipetted (10 times) using a glass pipette and then filtered twice over a filcon filter (30 mm) (DAKO). Separate medicons and filcons were used for each sample tissue. The cell suspension was centrifuged at 1500 rpm for 5 minutes and washed with ice cold PBS, centrifuged again, resuspended in PBS and then sorted using FACS.

Example 1
RT2 Glioma Cell Lines Stably Express GFP Over Many Cell Passages

GFP expression in transfected RT-2 cells was assayed by flow cytometry and fluorescence microscopy following successful transfection using the EGFP/pIRES construct. Samples of parental RT2 cells and transfected 3RT1 cells were cultured in parallel under identical conditions in G418 selection media. After the initial passage and after 21 passages, samples were prepared for FACS analysis. Samples were run in parallel at each time point, and the results are presented as fluorescence intensity histograms in FIG. 1, where the abscissa represents GFP fluorescence intensity and the ordinate represents relative cell counts. Note that the shift in the intensity peaks for the parental cells in 1A and 1B represents an artifact due to different gating parameters between the two time points for the low intensity background fluorescence seen in non-transfected RT2 cells. As can be seen, under the influence of G418 selection (1 mg/ml) the expression of GFP (98% of cells) was maintained beyond 21 passages (FIGS. 1C and 1D). Some cell clones demonstrated reversal of GFP expression over time even in the presence of G418 (data not shown). These clones were frozen, stored and not used for subsequent analysis.

Further, to address the question of G418 selection requirement for the maintenance of GFP expression, the transfected cell line, 3RT1 was treated with or without 1 mg/ml G418 for 30 days and the results are presented in FIG. 2. The parental RT2 cell line is included for reference (2A). The 3RT1 cell line maintained GFP expression without G418 through 3 passages (2B) and for over 30 days (2C). There is some loss of expression (approximately 10%) observed over 9 serial passages compared to 3RT1 cells treated with G418 (FIG. 2 D).

Example 2
In vitro Analysis Using Fluorescence Microscopy

The level of in vitro expression of GFP was analyzed using fluorescence microscopy and the results are given in FIG. 3. As can be seen, no difference in cellular morphology is seen when comparing the parental cell line, RT2 (3E) to the transformed cell line, 3RT1 (3D) by phase contrast microscopy. Using a GFP filter set from Chroma Technology Corporation, the difference between control RT2 (3B) and 3RT1 (3A) fluorescence is dramatic. No fluorescence was observed in the control cells whereas the 3RT1 cells were highly fluorescent. The GFP expression seems to be delocalized thoughout the cell body (FIG. 3C).

Example 3
Difference in the in vitro Growth Rates of Transfected and Control RT2 Cell Lines Studies were done to compare growth rates between parental RT2 cells (control) and the 3RT1 clones stably transfected with the EGFP/pIRES vector. Cells were plated in 96-well microtiter plates. At the indicated times, cells were prepared and analyzed for cell grow by using the CellTiter 96 Aqueous cell proliferation assay. The results are given in FIG. 4. As can be seen, according to MTS assays there is no significant difference in the in vitro growth rate of the transfected 3RT1 cells and control parental RT2 cells.

Example 4
RT2 Cells Stably Transfected with EGFP/pIRES Also Grow Tumors in Syngenic Rats The ability of RT2 cells stably transfected with EGFP/pIRES to grow tumors in syngenic rats was examined. The results showed that rats bearing either EGFP/pIRES transfected RT2 cells or parental RT2 tumors showed no significant differences in survival rates. Rats infused with parental RT2 control or the 3RT1 clone succumbed to brain tumors between 13–15 days post infusion of tumor cells (data not shown). 3RT1 tumor cells infused into rat brain and assayed for GFP expression in fresh thick 1 mm slices or paraformaldehyde fixed tissue following 13–15 days post tumor infusion are highly fluorescent (data not shown). Control tumors from parental RT2 cells show nonspecific background fluorescence in the fresh 1 mm thick slices. However, there was little background from control tumors in thin 50 micron sections of paraformaldehyde fixed tissue. GFP positive cells were seen in cortex away from tumor core. In addition, GFP positive cells and some tumor cells were seen in close association with brain vasculature. Individual tumor cells were seen beyond the host/tumor border and those associated with the vasculature may represent tumor cells within the Virchow-Robins space.

By comparison with phase contrast images of the same sections, dark structures in the fluorescence photomicrographs were noted to contain red blood cells within dilated vascular structures. Tumor cells were commonly found to be associated with these vascular structures and individual infiltrative tumor cells were readily identified.

Example 5
Retrieval and Identification of Tumor Cells which have Migrated from Tumor Core into Brain One of the main goals of this research is to monitor cell invasion beyond the tumor core. In order to do so, we retrieved and sorted the EGFP/pIRES expressing cells by fluorescence activated cell sorting. This technique allows not only identification but also recovery of the cells of interest for additional analysis. Fourteen days after tumor cell implantation, tissue samples from tumor core, adjacent brain, and the contralateral hemisphere were disaggregated and sorted from single cell suspensions by FACS. The resulting cell fractions were cultured for 2 weeks with or without G418, as indicated, then processed for flow cytometry to produce the fluorescence intensity histograms shown in FIG. 5. As can be seen, cells stably transfected with this vector can be successfully retrieved from host tissue and analyzed. Thus, use of the present invention provides access to individual tumor cells that have disseminated into distal areas of the brain. This invention is a unique and powerfull tool for the assessment of the molecular mechanisms which underlie local diffuse invasion and metastasis.

Example 6
U373 Human Glioms Cell Lines Stably Express GFP

GFP expression in transfected human glioma U373 cells was assayed by flow cytometry following successful transfection using the EGFP/pIRES construct. Samples of parental U373 cells and transfected U373-GFP cells were cultured in parallel under identical conditions in G418 selection media. After 3 cell passages, samples were prepared for FACS analysis. Samples were run in parallel at each time point, and the results are presented as fluorescence intensity histograms in FIG. 8, where the abscissa represents GFP fluorescence intensity and the ordinate represents relative cell counts. As can be seen, under the influence of G418 selection (1 mg/ml) the GFP is stably expressed in human U373 cells. Similar results were obtained with cells up to passage 20 (data not shown) indicating that GFP expression is stable indefinitely in this human cell line.

While the invention has been described in terms of its preferred embodiments, those skilled in the art will recognize that the invention can be practiced with modification within the spirit and scope of the appended claims. Accordingly, the present invention should not be limited to the embodiments; as described above, but should further include all modifications and equivalents thereof within the spirit and scope of the description provided herein.

References

[1] E. R. Laws Jr, W. J. Goldberg, J. J. Bernstein, Migration of human malignant astrocytoma cells in the mammalian brain: Scherer revisited. Int. J. Devi. Neurosci. 11 (1993) 691–697.

[2] M. R. Chicoine, D. L. Silbergeld, The in vitro motility of human gliomas increases with increasing grade of malignancy. Cancer 75 (1995) 2904–2909.

[3] M. R. Chicoine, D. L. Silbergeld, Assessment of brain tumor cell motility in vivo and in vitro. J. Neurosurg. 82 (1995b) 615–622.

[4] D. L. Silbergeld, M. R. Chicione, Isolation and characterization of human malignant glioma cells from histologically normal brain. J. Neurosurg. 86 (1997) 525–531.

[5] R. Bjerkvig, O. D. Laerum, G. J. Rucklidge. Immunocytochemical characterization of extracellular matrix proteins expressed by cultured glioma cells. Cancer Res. 49 (1989) 5424–5428.

[6] O. D. Laerum and M. L. Rosenblmn, Brain tumor cell invasion: present knowledge and future prospects, in: T. Miakelsen, R. Bjerkvig, O. D. Laerum, M. L.Rosenblum (Eds.), Brain Tumor Invasion: Biological, Clinical, and Therapeutic Considerations, Wiley-Liss, New York, 1998, pp. 449–455.

[7] J. J. Bemstein, W. J. Goldberg, E. R. Laws, Human malignant astrocytoma xenografts migrate in rat brain: A model for central nervous system cancer research. J. Neurosci. Res. 22 (1989) 134–143.

[8] T. A. Read, F. Thorsen, I. Garcia-Cabrera, A. Jorge, A Terzis, R. Bjerkvig, The growth of lacZ-transfected glioma cells in the central nervous system, in: T. Mikkelsen, R. Bjerkvig, O. D. Laerum, M. L. Rosenblum (Eds.), Brain Tumcor Invasion: Biological, Clinical, and Therapeutic Considerations, Wiley-Liss, New York, 1998, pp. 261–272.

[9] G. H. Vmce. H. Bouterfa, R. Goldbrunner, K. Roosen, J. C. Tonn, Fast blue, a fluorescent tracer in gloma cell culture, affects cell proliferation and motility. Neurosci. Lett. 233 (1997) 148–150.

[10] I. Garcia-Cabrera, K. Edvardsen, B. B. Tysnes, T. Read, R Bjerkvig, The lac-z reporter gene: a tool for in vitro studies of malignant glioma cell invasion. Invasion Metastasis 16 (1996) 107–115.

[11] T. Chishima, Y. Miyagi, X. Wang, H. Yamaoka, H. Shimada, A. R. Moossa, R. M. Hoffman, Cancer invasion and micrometastasis visualized in live tissue by green fluorescent protein expression. Cancer Res. 5 (1997) 2042–2047.

[12] A. N. Gubin, B. Reddy, J. M. Njoroge, J. L. Miller, Long-term, stable expression of green fluorescent protein in mammalian cells. Biochem. Biophys. Res. Commun. 262 (1997) 347–350.

[13] D. C. Prasher, Using GFP to see the light. Trends Genet. 11 (1995) 320–323.

[14] D. C. Prasher, V. K. Eckenrode, W. W. Ward, F. G. Prendergast, M. J. Connier, Primary structure of the Aequorea Victoria green-fluorescent protein. Gene 111 (1992) 229–233.

[15] S. X. Kain, M. Adams, A. Kondepudi, T. T. Yang, W. W. Ward, P. Kitts, Green fluorescent protein as a reporter of gene expression and protein localization. Biotechniques 19 (1995) 650–655.

[16] B. Ludin, A. Matus, GFP illuminates the cytoskeleton. Trends Cell Biol. 8 (1998) 72–77.

[17] L. Lybarger, D. Dempsey, G. H. Patterson, D. W. Piston, S. R. Kain, R. Chervenak, Dual-color flow cytometric detection of fluorescent proteins using single-laser (488-nm) excitation. Cytometry 31 (1998) 147–152.

[18] Misteli T and Spector D. L. Applications of the green fluorescent protein in cell biology and biotechnology. Nat. Biotechnol. 15 (1997) 961–964.

[19] A. B. Cubitt, R. Heir S. R. Adams, A. E. Boyd, L. A. Gross, R. Y. Tsien, Understading, improving and using green fluorescent proteins. Trends Biochemn. Sci. 20 (1995) 448–455.

[20] R. F. Kalejta, T. Shenk, A. J. Beavis, Use of a memnbrane-localized green fluorescent protein allows simultaneous identification of transfected cells and cell cycle analysis by flow cytometry. Cytometry 29 (1997) 286–291.

[21] G. N. Phillips Jr, Structure and dynamics of green fluorescent protein. Cuff. Opin. Struct. Biol. 7 (1997) 821–827.

We claim:

1. A pIRES/EGFP DNA vector construct.

2. The DNA vector construct of claim 1, wherein said DNA vector construct further comprises a gene of interest.

3. The vector construct of claims 2, wherein said gene of interest is selected from the group consisting of the tissue inhibitor of matrix metalloproteinase and tyrosine hydroxylase.

4. A cell stably transfected with the vector construct of claim 2.

5. The DNA vector construct of claim 1, wherein said DNA vector construct further comprises targeting sequences.

6. The DNA vector construct of claim 1, wherein said DNA vector construct further comprises a control element.

7. The vector construct of claim 1 wherein said vector construct further comprises a genetic control element which allows for expression of EGFP.

8. A cell stably transfected with the vector construct of claim 1.

9. A pIRES DNA vector construct which encodes a gene coding for a green fluorescent protein marker.

10. A reagent for assessing biological processes in real time, comprising a sufficient quantity of non-bacterial cells stably transfected with a green fluorescent protein marker in a suitable carrier medium, wherein transfection of said non-bacterial cells is carried out with a non-viral vector construct, and wherein said green fluorescent marker is encoded by a pIRES/EGFP DNA vector construct.

11. A method for monitoring a biological process in a host tissue, comprising the steps of
   providing to said host tissue a cell transfected with pIRES/EGFP; and
   monitoring GFP in said host tissue.

12. A method for monitoring biological processes in a host cell, comprising the steps of:
   transfecting said host cell with pIRES/EGFP; and
   monitoring GFP in said host cell.

13. An assay method for monitoring the effect of an agent on cells which have been stably transfected with pIRES/EGFP, wherein transfection of said cells is carried out with a non-viral vector construct, comprising the steps of:
   providing a host cell stably transfected with pIRES/EGFP;
   exposing said host cell to an agent;
   monitoring at least one phenomenon in said host cell wherein said phenomenon is detectable by detecting GFP fluorescence.

14. The assay method of claim 13 wherein said agent is a toxin.

15. The assay method of claim 13 wherein said agent is a drug.

16. The assay method of claim 13 wherein said agent is an infectious agent.

17. The assay method of claim 13 wherein said phenomenon is cellular migration.

18. The assay method of claim 13 wherein said phenomenon is cellular location.

19. The assay method of claim 13 wherein said phenomenon is cellular shape.

20. The cell of claim 1 wherein said non-viral vector construct is pIRES/EGFP.

21. A host cell stably transfected with a green fluorescent protein marker wherein transfection of said host cell is carried out with a non-viral vector construct, and wherein said non-viral vector construct is pIRES/EGFP.

22. The host cell of claim 21 wherein said host cell is a glioma cell.

23. The host cell of claim 21 wherein said host cell is a tumor cell.

24. The host cell of claim 21 wherein said host cell is a stem cell.

25. The host cell of claim 21 wherein said host cell is a non-bacterial infectious agent.

* * * * *